(12) United States Patent
Rudge et al.

(10) Patent No.: US 6,223,747 B1
(45) Date of Patent: May 1, 2001

(54) CONDOMS

(75) Inventors: Janette Mary Rudge, Suffolk; Janette Louise Rogers, Ketton, both of (GB)

(73) Assignee: LRC Products Limited, Broxbourne (GB)

( * ) Notice: Subject to any disclaimer, the term of this patent is extended or adjusted under 35 U.S.C. 154(b) by 0 days.

(21) Appl. No.: 09/125,190

(22) PCT Filed: Feb. 14, 1997

(86) PCT No.: PCT/GB97/00428

§ 371 Date: Aug. 13, 1998

§ 102(e) Date: Aug. 13, 1998

(87) PCT Pub. No.: WO97/30668

PCT Pub. Date: Aug. 28, 1997

(30) Foreign Application Priority Data

Feb. 22, 1996 (GB) .................................................. 9603777

(51) Int. Cl.⁷ .......................................................... A61F 6/04
(52) U.S. Cl. ............................................ 128/844; 128/918

(58) Field of Search ..................................... 128/842, 844, 128/918; 604/347–353

(56) References Cited

U.S. PATENT DOCUMENTS

| 5,458,114 | * | 10/1995 | Herr | 128/844 |
| 5,515,862 | * | 5/1996 | Artsi | 128/844 |
| 5,638,829 | * | 6/1997 | Najor | 128/842 |
| 5,855,206 | * | 1/1999 | Ireland | 128/844 |

* cited by examiner

*Primary Examiner*—Michael A. Brown
(74) *Attorney, Agent, or Firm*—Sidley & Austin

(57) ABSTRACT

A condom has a ring (6) adjacent the open end (1) for expanding the condom to a maximum diameter to maintain the open end outside the vagina, and a tubular portion (3) extending between the ring and the closed end is of a size to form a loose fit around the penis and is formed with a series of circumferential grooves (5), e.g. 3 to 5 grooves around 0.8 cm wide and 1.0 cm deep, so that the condom naturally folds in a bellows like manner for the condom to collapse to a substantially flat condition prior to use.

13 Claims, 4 Drawing Sheets

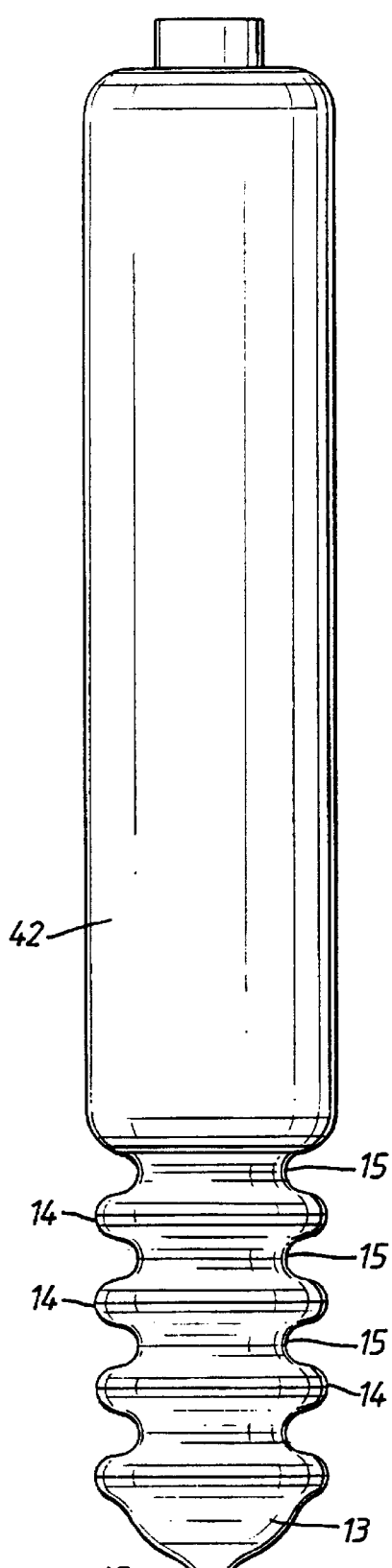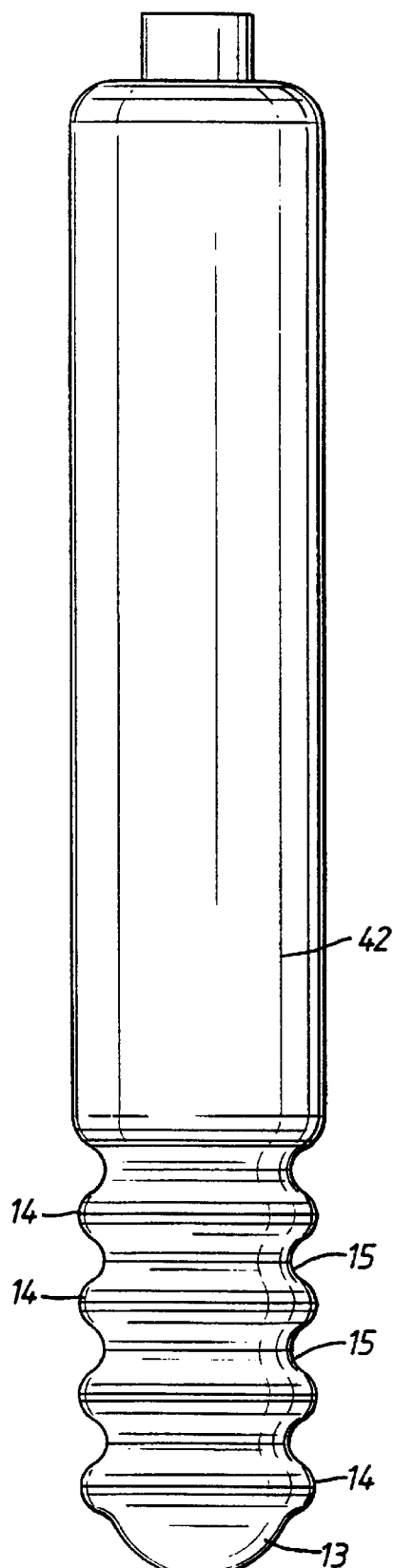

CONDOMS

This invention relates to condoms and it is especially concerned with condoms which will line the wall of the vagina and unlike male condoms which are initially donned by the male and fit closely around the penis are dimensioned to loosely enclose the penis at least over the length of the condom received within the vagina. For convenience such condoms are referred to wherein as "female condoms".

These is currently marketed a female condom consisting of a flexible thin-walled bag-like liner with a closed end and an open end opposite the closed end. The liner is formed from two sheets of plastic material sealed together at their edges, and a solid ring of relatively stiff plastic material is fixed to the liner at the open end and acts to hold the mouth of the liner open. The primary function of the stiff ring is to maintain the open end of the condom outside the vagina. The liner is provided with a second relatively stiff ring which is of smaller diameter than the first ring and is inserted loosely into the liner. This second ring is intended to hold the closed end of the liner in place adjacent the uterus.

The known female condom is not convenient to use and its insertion, particularly due to the need to ensure correct positioning of the loose inner ring, is rather awkward and frequently necessitates an undesirable interruption in the process of sexual activity leading to coitus. Due to the liner being formed from sheet material and the inclusion of the loose ring, the liner has a natural tendency to collapse laterally, which does not facilitate its insertion into the vagina.

The present invention aims to provide a female condom which is more convenient to use without requiring prior application to the penis, and according to the invention these is provided a female condom comprising a closed end and an open end, a ring adjacent to the open end for expanding the condom to a maximum diameter at the location of the ring to maintain the open end outside the vagina, and a tubular wall portion extending between the closed end and the ring, said wall portion being of a size to form a loose fit around the male penis and being formed with a series of circumferential grooves of such a depth that the tubular wall readily folds in a bellows or concertina-like manner whereby the condom collapses longitudinally to a substantially flat condition.

There have been numerous proposals of condoms which are corrugated in some manner, and there have been numerous proposals of condoms with rings or flanges which remain outside the vagina, but the particular combination of a large ring and a grooved wall portion as provided in a condom in accordance with the invention, and which results in an especially convenient and efficacious condom, has not been previously suggested. Furthermore, the condom of the invention is suitable for large scale production by conventional manufacturing processes, whereas the complexities of many of the proposals contained in the prior art would involve manufacturing difficulties making economic production on a commercial scale extremely difficult and in some cases impossible.

The number of grooves included in the tubular wall portion need not be large and very satisfactory results can be obtained with 3 to 5 grooves. Four grooves are currently preferred. Suitably the depth of the grooves is in the range of 0.5 cm to 1.5 cm, and the presently preferred depth is between 0.8 cm and 1.2 cm. In a preferred embodiment, the grooves are formed with intervening circumferential ridges, and the width or the grooves is substantially equal to the width of the ridges e.g. 0.5 cm to 1.0 cm, preferably about 0.8 cm. The grooves and ridges can be wider, however, such as up to about 1.5 cm e.g. around 12 or 13 cm and ridges are preferably formed with the bottoms of the grooves and the crests of the ridges substantially semi-circular in cross-section or shaped to merge smoothly with each other to preclude any sharp discontinuities and potential weaknesses along the tubular portion.

The condom of the invention is conveniently manufactured by coating a former with latex or a polymer and allowing the coating material to cure if required before the condom is stripped from the former. The coating can be applied by spraying or by a dip moulding process in which a shaped former is dipped into a liquid bath e.g. of latex, liquid polyurethane, or other polymer composition, and withdrawn carrying with it a thin layer of the coating material. The manufacture by dip moulding may be by multiple dips into the same or successive liquid baths and this can be used to control the thickness of the moulded condom. The former is provided with annular grooves for forming the circumferential grooves of the condom and due to natural flow effects during the dipping process the liquid coating at the bottoms of the grooves can be slightly thicker than on the other surface portions of the former. This may result in the wall thickness of the condom being increased at the bottoms of the grooves e.g. by around 10% to 50%, which can assist the natural tendency for the condom to collapse longitudinally and for the radial undulations to be maintained during the folding process.

The ring adjacent to the open end of the condom is conveniently and preferably integrally formed with the tubular wall. Alternatively the condom may comprise a separately made rubber ring, e.g. a solid silicone rubber ring or a ring formed from rubber tube which has desirable characteristics of resilient flexibility and can ensure a good level of comfort. The separate ring may be securely attached to the condom wall and can be embedded in the material of the wall by locating the ring onto the former before it is coated with material to form the condom. Alternatively the ring could be secured to the condom after it has been formed.

In use, a condom in accordance with the invention can be held in its longitudinally collapsed substantially flat form over the vaginal opening, and the closed end of the condom can be pushed into the vagina by the penis as it penetrates the vagina at the beginning of sexual intercourse, the ring which is preferably at least about 7 cm in diameter ensuring that the open end remains outside during initial insertion and throughout the coital act.

According to one embodiment of the invention, the female condom includes a second ring of smaller diameter attached to the condom wall a short distance beyond the larger ring. This second ring, which, in accordance with a method known per se, can be provided by rolling down a portion of material coated into the former before it is fully cured, is dimensoned to have a close fit around the penis so that when the penis is withdrawn it removes the condom from the vagina.

Female condoms embodying the invention are more convenient to use than those currently available.

To facilitate a clear understanding of the invention some particular embodiments will now be described with reference to the accompanying drawings, in which.

Figure 1:
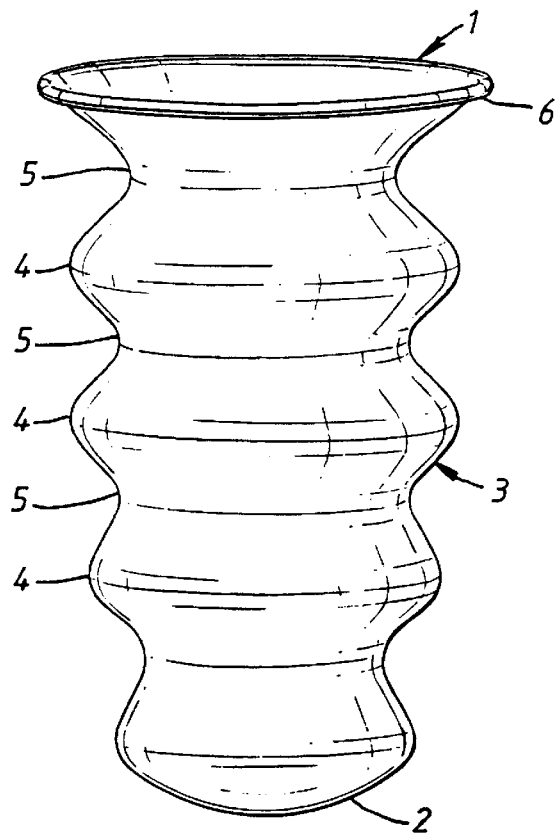
FIG. 1 is a side view of a female condom embodying the invention.
Figure 2:
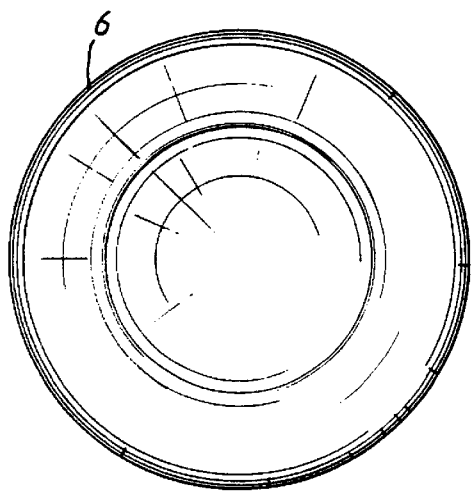
FIG. 2 is a plan view of the condom shown in FIG. 1.
Figure 7:
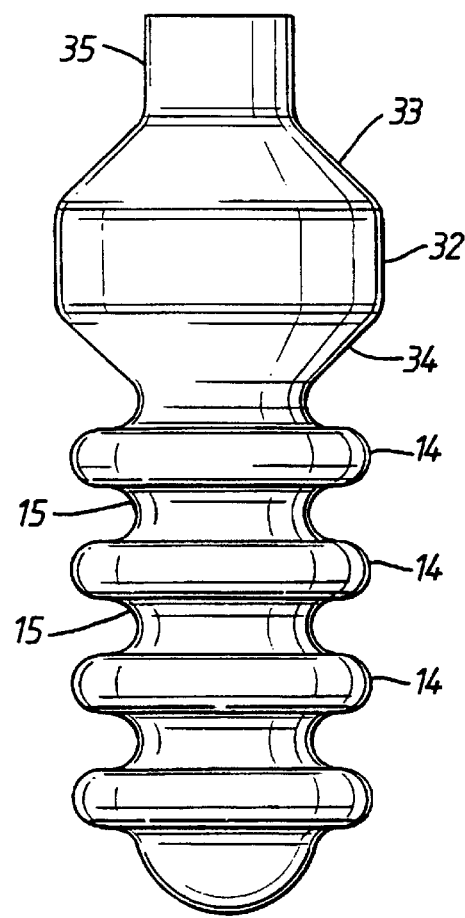
Figure 5:
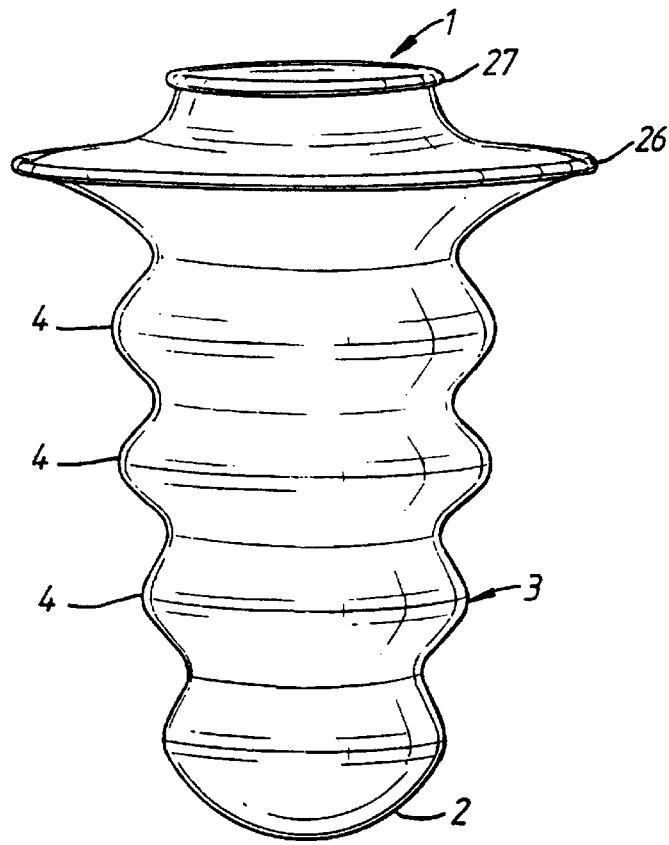
FIG. 5 is a side view of a second female condom according to the invention.
Figure 6:
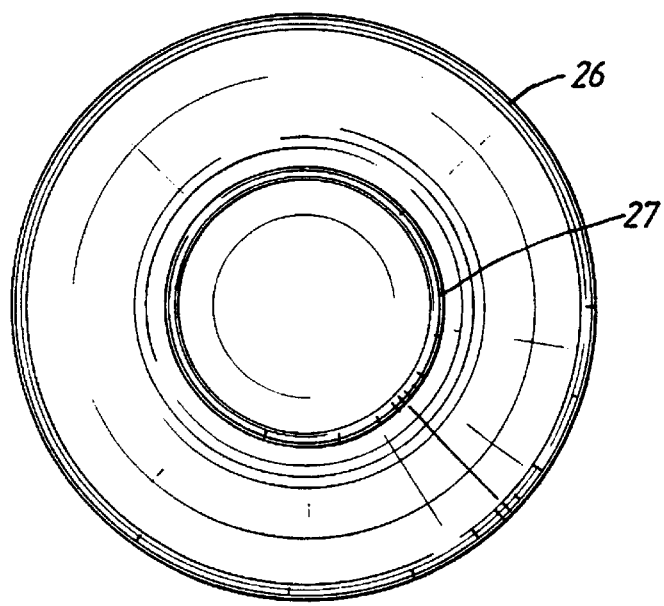
FIG. 6 is a plan view of the condom shown in FIG. 5.

FIG. 7 is a side elevation of a former used to manufacture the condom of FIGS. 5 and 6; and FIGS. 8 and 9 show in side elevation two modified formers suitable for manufacturing condoms generally similar to that or FIGS. 1 and 2.

Figure 4:
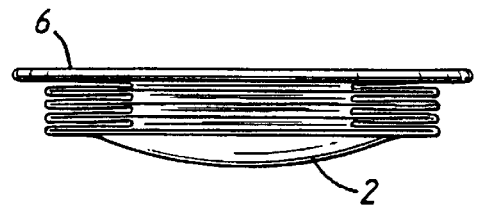
FIG. 4 shows the condom in its flat folded condition.
Figure 3:
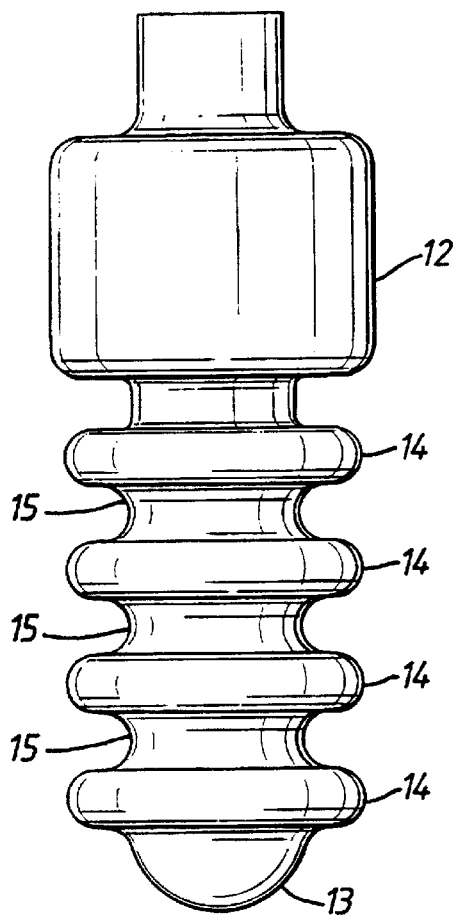
FIG. 3 is a side elevation of a former used to manufacture the condom of FIGS. 1 and 2.

The female condom illustrated in FIGS. 1, 2 and 4 is formed of latex or polyurethane by a dip moulding process using the former of FIG. 3. The condom has an open end 1, a closed end 2 and a tubular wall 3 interconnecting the ends and formed with radial undulations defined by alternate circumferential ridges 4 and grooves 5. At the open end 1 the condom is provided with a relatively stiff but flexible ring 6 which may be silicone rubber or made of tubular rubber, but can be conveniently formed integrally with the tubular wall. The ring has a diameter of about 7 cm and it radially expands the condom to a maximum diameter. The former includes an upper moulding portion 12 fo cylindrical form and having a diameter approximately equal to that of the condom ring 6. At its lower end the former has a substantially hemispherical dome-shaped portion 13 for forming the closed end wall 2 of the condom. Between the portions 12 and 13 are a series of annular ridges 14 which define annular grooves 15 for forming the ridges 4 and grooves 5 of the condom, respectively. The crests of the ridges 14 and the bottoms of the radial grooves 15 are substantially semi-circular in cross-section and the grooves are about 1.0 cm deep and 0.8 cm wide. The former is dipped into a bath of e.g. liquid latex and becomes coated to a level a little below the upper edge of the portion 12. The thickness of material coating the bottoms of the grooves is typically 0.04 to 0.10 mm compared with a thickness of 0.02 to 0.06 mm at the ridge tops, although the thickness may be up to 0.12 mm at the grooves and up to 0.1 mm at the ridges. After curing sufficiently, some of the material coating the portion 12 is rolled down from its upper edge to form a bead which becomes the ring 6 fo the condom. If required additional bead material could be applied over the part of the dipped material to be rolled to form the bead. When the latex is cured, the condom is stripped form the former, and after appropriate testing it is collapsed longitudinally to the flat condition shown in FIG. 4, which is readily achieved since the condom has a natural tendency to fold in a bellow-like manner due to the grooves 4. The condom is then packaged. When it is to be used, it is removed from the package and held in the flat condition over the vagina to be inserted as previously described.

The condom of FIGS. 5 and 6 and the former of FIG. 7 are for the most part the same as those described above and only the modifications will be described. The condom has a large ring 26 and beyond it at the open end a smaller ring 27 having a diameter about half that of the large ring. The former has an upper portion with a cylindrical section 32 located between frusto-conical sections 33,34 and a neck portion 35 above the upper frusto-conical section 33. When provided with a dipped coating, the material coating the neck portion 35 is rolled down from its upper edge to form a bead which constitutes the smaller ring 27 of the condom. After the condom has been stripped from the former, a separate solid rubber ring is inserted to provide the larger ring 26. If preferred the rubber ring can be located onto the cylindrical section 32 of the former before it is coated so that the ring becomes embedded in the condom material during the dip moulding process.

The condom is used in essentially the same way as the first embodiment. However, when used to insert the condom into the vagina the penis is passed through the small ring 27 as well as the larger ring 26 which always remains outside the vagina. When the penis is subsequently withdrawn, as it is gripped lightly by the ring 27, the condom will be simultaneously withdrawn form the vagina.

Although the condoms described herein have for convenience been referred as "female condoms" it should be understood that this term has been used only to mean that the portion of the condom between the closed end and the expansion ring will be a loose fit around the penis, and if preferred by users, there is no reason why the condom should not be placed over the penis of the make before insertion into the vagina of the female.

The formers of FIGS. 8 and 9 are particularly suited to the manufacture of condoms as shown in FIGS. 1 and 2 and having integral rings at their open ends. Above the lower grooved section each former has a substantially uniform cylindrical shape with a diameter of about 7 cm. This cylindrical portion can be coated with material which is rolled up from its free edge before the material had dried or cured in order to form the integral ring. In the former of FIG. 8 the bottoms of the annular grooves 15 have a radius of curvature of about 6 mm and the crests of the annular ridges 14 between the grooves have a similar radius of curvature. The diameter of the former at the bottoms of the grooves is about 41 mm and at the crests of the ridges the diameter is about 65 mm, the depth of the grooves being about 12 mm. The width of the ridges and of the grooves, measured at half the depth of the grooves where the curvature changes from concave to convex is 12 mm. In the former of FIG. 9, the grooves 15 are shallower, the diameter of the former at the bottoms of the grooves 15 being 50 mm and the diameter at the crests of the ridges 14 being 65 mm so the groove depth is 7.5 mm. The radius of curvature at the bottoms of the grooves and at the crests of the ridges is 7 mm. The edge profile of the grooved section of the former is more sinusoidal than with the formers of the previous embodiments. The width of the ridges and the grooves, again measured at half the groove depth where the curvature changes form concave to convex is about 13 mm. The formers of FIGS. 8 and 9 have small nippies 45 at the centre of the lowermost dome-shaped portions 13 for producing shallow pockets at the closed ends of the condoms produced on these formers. It will be appreciated that the condoms moulded on the formers of FIGS. 8 and 9 will have dimensions which are essentially the same as those or the formers.

What is claimed is:

1. A condom comprising a closed end and an open end, a ring at or adjacent to the open end, the ring expanding the condom to its largest diameter at the location of the ring in order to maintain the open end outside the vagina during sexual intercourse, said tubular wall portion being of a size to form a loose fit around the penis, wherein the tubular wall portion is formed with a series of circumferential grooves of such a depth that the tubular wall readily folds in a bellows or concertina manner for the condom to collapse longitudinally into a substantially flat condition, and the ring expands the condom to a maximum diameter of at least about 7 cm.

2. A condom according to claim 1, wherein the grooves are 3 to 5 in number.

3. A condom according to claim 1 wherein circumferential ridges are located between the grooves, the ridges and grooves being provided over substantially the entire length of the tubular portion.

4. A condom according to claim 3, wherein the width of the grooves is substantially equal to the width of the ridges.

5. A condom according to claim 4 wherein the bottoms of the grooves and the crests of the ridges are substantially semi-circular in cross-section.

6. A condom according to claim 1, wherein the width of the grooves is in the range of 0.5 to 1.5 cm.

7. A condom according to claim 1, wherein the depth of the grooves is in the range of 0.8 to 1.2 cm.

8. A condom according to claim 1, wherein the depth of the grooves is in the range of 0.8 to 1.2 cm.

9. A condom according to claim 1, wherein the wall thickness at the bottom of the grooves is greater than the wall thickness of the tubular wall portion between the bottoms of the grooves.

10. A condom according to claim 1, wherein at least the tubular portion of the condom is formed by dip moulding.

11. A condom according to claim 10, wherein the ring is formed by rolling up material coated onto a former on which the tubular portion of the condom is formed.

12. A condom according to claim 1, wherein the ring is near but spaced from the open ring and a second ring of smaller diameter than the expansion ring is located at the open end of the condom.

13. A condom according to claim 12, wherein the diameter of the smaller ring is approximately half that of the expansion ring.

* * * * *